(12) United States Patent
Cho

(10) Patent No.: US 12,186,458 B1
(45) Date of Patent: Jan. 7, 2025

(54) PORTABLE VAPOR GENERATING DEVICES AND METHODS

(71) Applicant: The Government of the United States of America, as represented by the Secretary of Homeland Security, Washington, DC (US)

(72) Inventor: Inho Cho, Egg Harbor Township, NJ (US)

(73) Assignee: The Government of the United States of America, represented by the Secretary of Homeland Security, Washington, DC (US)

( * ) Notice: Subject to any disclaimer, the term of this patent is extended or adjusted under 35 U.S.C. 154(b) by 1116 days.

(21) Appl. No.: 16/367,782

(22) Filed: Mar. 28, 2019

(51) Int. Cl.
*A61L 9/03* (2006.01)
*A01K 15/02* (2006.01)

(52) U.S. Cl.
CPC ............... *A61L 9/03* (2013.01); *A01K 15/02* (2013.01); *A61L 2209/135* (2013.01)

(58) Field of Classification Search
CPC ...... A01K 15/02; A61L 9/03; A61L 2209/135
USPC ........................................................ 392/386
See application file for complete search history.

(56) References Cited

U.S. PATENT DOCUMENTS

| | | | |
|---|---|---|---|
| 6,812,834 B2 | 11/2004 | Lyon et al. | |
| 8,011,224 B2 * | 9/2011 | Kendler | G01N 1/405 |
| | | | 95/82 |
| 8,395,086 B2 * | 3/2013 | Combes | G01N 30/08 |
| | | | 73/25.05 |
| 8,668,873 B2 * | 3/2014 | Almirall | G01N 33/227 |
| | | | 422/527 |
| 9,412,573 B2 * | 8/2016 | Almirall | G01N 27/622 |
| 10,274,469 B2 * | 4/2019 | Brasfield | G07C 9/10 |
| 10,365,075 B2 * | 7/2019 | Apblett | F42B 12/207 |
| 10,813,342 B2 * | 10/2020 | Maughan | A01K 15/02 |
| 10,866,166 B2 * | 12/2020 | Shaikh | B01D 53/0407 |
| 10,959,406 B2 * | 3/2021 | Campbell | A01K 15/02 |
| 11,220,386 B2 * | 1/2022 | Steed | A01K 15/02 |
| 11,458,451 B2 * | 10/2022 | Shaikh | B01J 20/3293 |
| 2007/0266771 A1 * | 11/2007 | Goldson | G01N 33/497 |
| | | | 73/31.07 |
| 2008/0295783 A1 * | 12/2008 | Furton | F41H 11/132 |
| | | | 73/1.01 |

(Continued)

FOREIGN PATENT DOCUMENTS

| | | |
|---|---|---|
| WO | 2008118573 A2 | 10/2008 |
| WO | 2008118573 A3 | 10/2008 |
| WO | 2014181118 A1 | 11/2014 |

OTHER PUBLICATIONS

WO2007/057901 (Year: 2023).*
EP0104758 (Year: 2023).*
CN106659279 (Year: 2023).*

*Primary Examiner* — Nathaniel E Wiehe
*Assistant Examiner* — Frederick F Calvetti
(74) *Attorney, Agent, or Firm* — Lavanya Ratnam; Robert W. Busby; Kelly G. Hyndman

(57) ABSTRACT

Various embodiments of the present invention are directed towards a device and method relating to heating a sample. For example, a device includes a housing to support a sample including a trace of an explosive. A power supply is coupled to the housing to provide power to a heating element coupled to the housing. The heating element is configured to heat the sample to generate a vapor of at least one ingredient of the trace.

19 Claims, 3 Drawing Sheets

(56) References Cited

U.S. PATENT DOCUMENTS

| | | | |
|---|---|---|---|
| 2009/0145369 A1* | 6/2009 | Lumbroso | A61K 49/0008 |
| | | | 119/421 |
| 2016/0174525 A1* | 6/2016 | DeGreeff | A01K 15/02 |
| | | | 119/712 |
| 2016/0255811 A1* | 9/2016 | Campbell | A01K 15/02 |
| 2018/0055013 A1* | 3/2018 | Daley | A01K 15/02 |
| 2019/0184370 A1* | 6/2019 | Shaikh | B01J 20/28083 |
| 2019/0186878 A1* | 6/2019 | Apblett | F42B 8/28 |
| 2020/0054777 A1 | 2/2020 | Burns et al. | |
| 2020/0296932 A1 | 9/2020 | Daley et al. | |
| 2021/0187474 A1* | 6/2021 | Shaikh | C06B 23/00 |
| 2021/0251188 A1* | 8/2021 | Giles | A01K 15/02 |

\* cited by examiner

PORTABLE VAPOR GENERATING DEVICES AND METHODS

STATEMENT OF GOVERNMENT INTEREST

The present invention was made by one or more employees of the United States Department of Homeland Security in the performance of official duties, and, thus the claimed invention may be manufactured, used, licensed by or for the United States without the payment of any royalties thereon.

FIELD OF THE INVENTION

The present invention relates generally to the field of vapor generation, and more specifically to the field of vapor generation using a portable housing.

BACKGROUND OF THE INVENTION

Canines are capable of detecting explosives at low thresholds, such as by alerting to training materials containing trace levels of explosives. Although canines can be trained in a static laboratory setting using lab-based bulky stationary equipment, dynamic real-world testing can be challenging or impossible using such equipment, such as testing scenarios involving a decoy passenger who is unaware of carrying training materials for a canine to detect. Furthermore, training materials can cross-contaminate training environments, or can fail to provide enough odor for a canine to positively alert.

SUMMARY OF THE INVENTION

In an example embodiment, a device includes a housing to support a sample including a trace of an explosive. A power supply is coupled to the housing, and a heating element is coupled to the housing, configured to heat the sample to generate a vapor of at least one ingredient of the trace. In another example embodiment, a method includes applying a trace of an explosive to a sample, and heating the sample for a predefined duration to generate a vapor of at least one ingredient of the trace. In yet another example embodiment, a method includes placing a housing, containing a sample including a trace of an explosive, in a canine training environment, heating the sample to generate a vapor of at least one ingredient of the trace, and determining whether a canine alerts to the housing.

Other features and aspects of the invention will become apparent from the following detailed description, which taken in conjunction with the accompanying drawings illustrate, by way of example, the features in accordance with embodiments of the invention. This summary is not intended to identify key or essential features of the claimed subject matter, nor is it intended to limit the scope of the invention, which is defined solely by the claims attached hereto.

BRIEF DESCRIPTION OF THE DRAWINGS

One or more example embodiments of the present invention are described in detail with reference to the following drawings. These drawings are provided to facilitate understanding of the present invention and should not be read as limiting the breadth, scope, or applicability thereof. For purposes of clarity and ease of illustration, these drawings are not necessarily made to scale.

These drawings are not intended to be exhaustive or to limit the invention to the precise form(s) disclosed. It should be understood that the present invention can be practiced with modification and alteration, and that the invention is limited only by the claims and the equivalents thereof.

DETAILED DESCRIPTION OF THE INVENTION

Example embodiments described herein are configured to generate miniscule amounts of true vapor odorants from real explosives, in as little as a few seconds. A trace quantity of an explosive is deposited on a surface of a sample, e.g., an inert material, which is heated according to various heating rates or profiles, to create vapors spontaneously or on demand to serve as, e.g., odorants available to detection canines. This device can be used to study detection limit of the odorant(s) emitted from a targeted chemical compound. The device can be used for static or dynamic canine training operations, such as passenger screening. For example, on a dynamic test, a decoy passenger can carry the device and self-activate the device, or have the device remotely/automatically activated without knowledge or input by the decoy passenger, to release explosives odorants to test canine detection of person-borne explosives.

Figure 1:
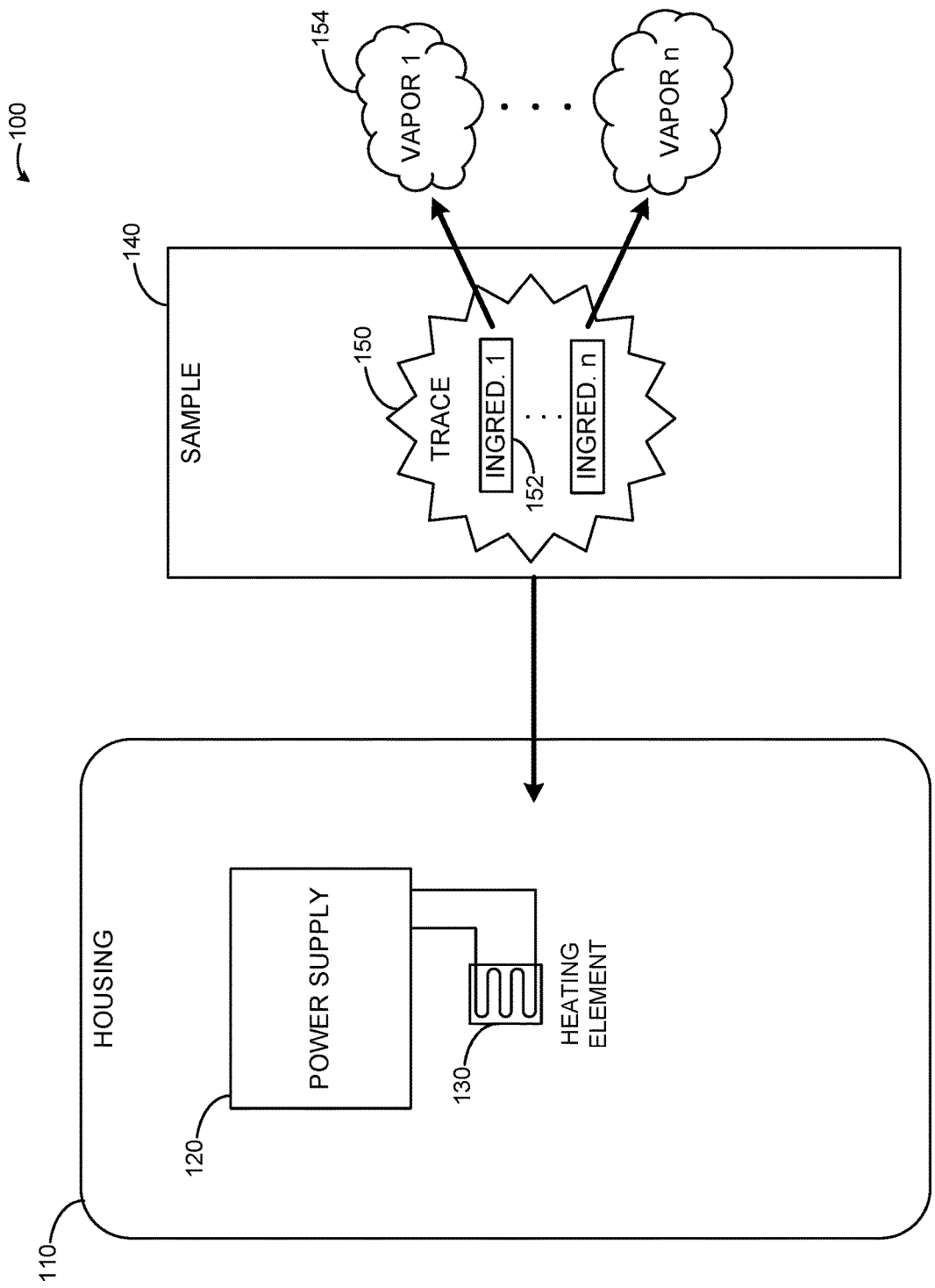
FIG. 1 illustrates a device including heating element according to an example embodiment.

FIG. 1 illustrates a device 100 including heating element 130 according to an example embodiment. A housing 110 is configured to support a sample 140 including a trace 150 of an explosive. The power supply 120 is coupled to the housing, to provide power to the heating element 130. The heating element 130 is coupled to the housing and configured to selectively heat the sample 140 to generate a vapor 154 of at least one ingredient 152 of the trace. In the illustrated example, the sample 140 is removable/replaceable from the housing 110. In other examples, the sample 140 can be integrated with the housing 110.

The trace 150 includes multiple ingredients 152. The heating element 130 can be selectively controlled by the device 100 to target a specific ingredient 152, so that the device 100 generates a vapor 154 corresponding to the targeted ingredient 152.

In an example embodiment, the housing 110 is provided as a static-dissipative polypropylene container having dimensions of 5.5 inches wide by 2.75 inched deep by 1.5 inches high. The static-dissipative housing 110 enables the device to accommodate samples 140 while minimizing risk of static discharge, and to accommodate samples 140 such as fine powders without generating static electricity to cause the powder to adhere to the housing 110.

In the illustrated embodiment, the sample 140 is provided as a sheet of fiberglass. Fiberglass is inert to avoid reacting with the trace 150, or other substances such as a solvent used to dissolve an explosive to generate a solution deposited onto the sample 140 as a trace 150. Fiberglass sample 140 also resists reacting to heat, because fiberglass comprises glass fibers that are highly heat-resistant. The sample 140 also is configured to provide physical properties that enable it to accommodate varying types of traces 150. For example, sample 140 can absorb or otherwise accommodate traces 150 in the form of solutions, liquids, powders, and solids (e.g., by mechanically wiping the solid onto the sample 140, to enable a surface roughness texture of the sample 140 to cause deposition of the trace 150 as a smear). The porous texture of the sample 140 also facilitates dispersing and wicking away of a solvent used in a liquid (solution, suspension, etc.) of trace 150.

In another embodiment, the sample 140 can be provided as a stick of material, inserted into a sleeve-style housing 110 to position an end of the stick proximate to the heating element 130 (in contrast to the illustrated sample that positions a central portion of the sample proximate to the heating element 130). The stick sample can be provided as a polyimide material, which is permeable to accept the trace 150, and heat resistant to resist reacting when the heating element 130 applies heat. The stick sample positioned in the sleeve-style housing 110 enables the device 100 to serve as a handheld wand unit. Regardless of the particular dimensions and layout of the housing 110 and other features, the device 100 can be carried by a decoy user as part of a canine training session, who can manually activate (or have a remote coordinator remotely activate) the device on-the-move, to deploy target odorant plumes of vapor without needing to remove the device from the user, and without needing to hide the device in a hiding location at the site of the training session. In other examples, a decoy user can unknowingly carry a device, which can be remotely triggered, or automatically triggered (e.g., by a controller implementing a timer delay or other heating profile), without knowledge of the decoy user, to establish a double-blind testing scenario. Such double-blind testing ensures that the decoy user is unaware of whether the decoy user is being used for testing in a given scenario, and therefore does not inadvertently signal body language or provide other physical cues which could inadvertently enable a canine to alert to the physical cues of the decoy user, such that the canine focuses on odor/vapor detection.

In the illustrated embodiment, the trace 150 is added to the sample 140 by doping the sheet of fiberglass with a solution of an explosive, e.g., explosive dissolved in a solvent. In an example, an explosive such as Homemade Explosive (HME) is dissolved using appropriate solvent to make an explosive solution. The sheet of fiberglass sample 140 also can be used to contain a powdered sample deposited beneath or on top of the sheet of fiberglass sample 140. In other examples, the trace 150 can be generated as a suspension, e.g., breaking down the explosive into small pieces (using a cryogenic technique) or a fine powder, and mixed with a carrier such as water to create the suspension, which then is applied to the sample 140 as the trace 150. As with a solution, a concentration of the suspension can be varied to provide a level of concentration of the trace 150 sufficient to generate, when heated, a plume of vapors appropriate for a given training scenario.

In an example embodiment, the power supply 120 is provided as a single nine volt (9V) battery, connected in series with a manual switch (not shown in FIG. 1; see FIG. 2) and the heating element 130. In another embodiment, the power supply 120 is provided as two series-connected 9V batteries, for additional power compared to a single 9V battery. Other examples can use various types of power sources, such as rechargeable battery packs.

The heating element 130 can be provided as a resistive coil. In other examples, the heating element 130 can be provided as a heating pad, such as a polyimide heating pad, whose size and shape can be customized to provide coverage for heating the sample 140, e.g., as a rectangular strip of heating pad shaped 1 inch wide by 3 inches long. The heating element 130 can be sized to cover a portion of the sample 140, such as that portion containing a trace 150. In other embodiments, the heating element 130 can be sized to substantially cover the entirety of the sample 140.

Heat can be applied to target various characteristics, e.g., the molecular weight and/or vapor pressure, of a given ingredient 152 of the trace 150. The device 100 can be configured to target one particular type of ingredient 152 in the trace 150, by vaporizing that ingredient 152 during the test to generate a corresponding vapor 154. For example, the power supply 120 can be limited to a given power output to cause the heating element 130 to generate a desired level of heating. A temperature sensor (not shown in FIG. 1) can be coupled in series with the heating element 130, and used to limit the heat output of the heating element 130 to generate a temperature consistent with targeting the specific ingredient 152.

The device 100 also can pre-heat (e.g., prior to generating a vapor 154 which is intended to be detected by a canine) the sample 140, e.g., at temperatures below the targeted temperature of the desired ingredient/vapor, to achieve various benefits. For example, the pre-heating can be used to vaporize and dissipate away a non-targeted ingredient, to thereby leave a bouquet of plumes including a targeted ingredient 152, and temperature can then be used to heat that remaining ingredient 152 corresponding to the targeted vapor 154, without risk of generating vapors from untargeted ingredients which vaporize at temperatures lower than the target temperature. The temperature of the heating element 130 can be limited to not exceed the target temperature, to avoid causing vapors from other untargeted ingredients that would start vaporizing at even higher temperatures. The device 100 generates a quick burst of intense heat, or a gradual increase of temperature, or any combination of heat delivery approaches as desired, such as by a pulse generator circuit element. For example, a gradual delivery of lower temperatures can be applied by manually switching on a single 9V battery, and then a burst of higher temperatures can be applied by manually switching on a second 9V battery in series with the first.

A given approach of heat by the heating element 130 depends on various factors, such as characteristics of the threat/trace 150 that is to be activated, and whether it contains target ingredients 152 that are easily vaporized, or if more heat and/or time is needed to activate the target ingredients. Different component ingredient molecules release in different ways, some at low vapor pressure corresponding to a boiling point characteristic of that ingredient. Other ingredients, e.g., those of low molecular weight/high vapor pressure, can be released without application of heat. For example, trace 150 can be provided as an explosive, which includes multiple ingredients 152 such as cyclotrimethylenetrinitriamine (RDX) solution. When heat is applied to the explosive trace 150, the highly volatile vapors 150 corresponding to solvents are vaporized first, followed after a duration of additional heating, by the RDX vapor. Accordingly, the device 100 can be used to selectively target some vapors for training a canine to alert, without releasing every vapor to inadvertently encourage the canine to alert on every ingredient. Alternatively, the device 100 can be used to train the canine to alert on all ingredients, by selectively generating vapors for all of the ingredients, either simultaneously or in series.

Figure 2:
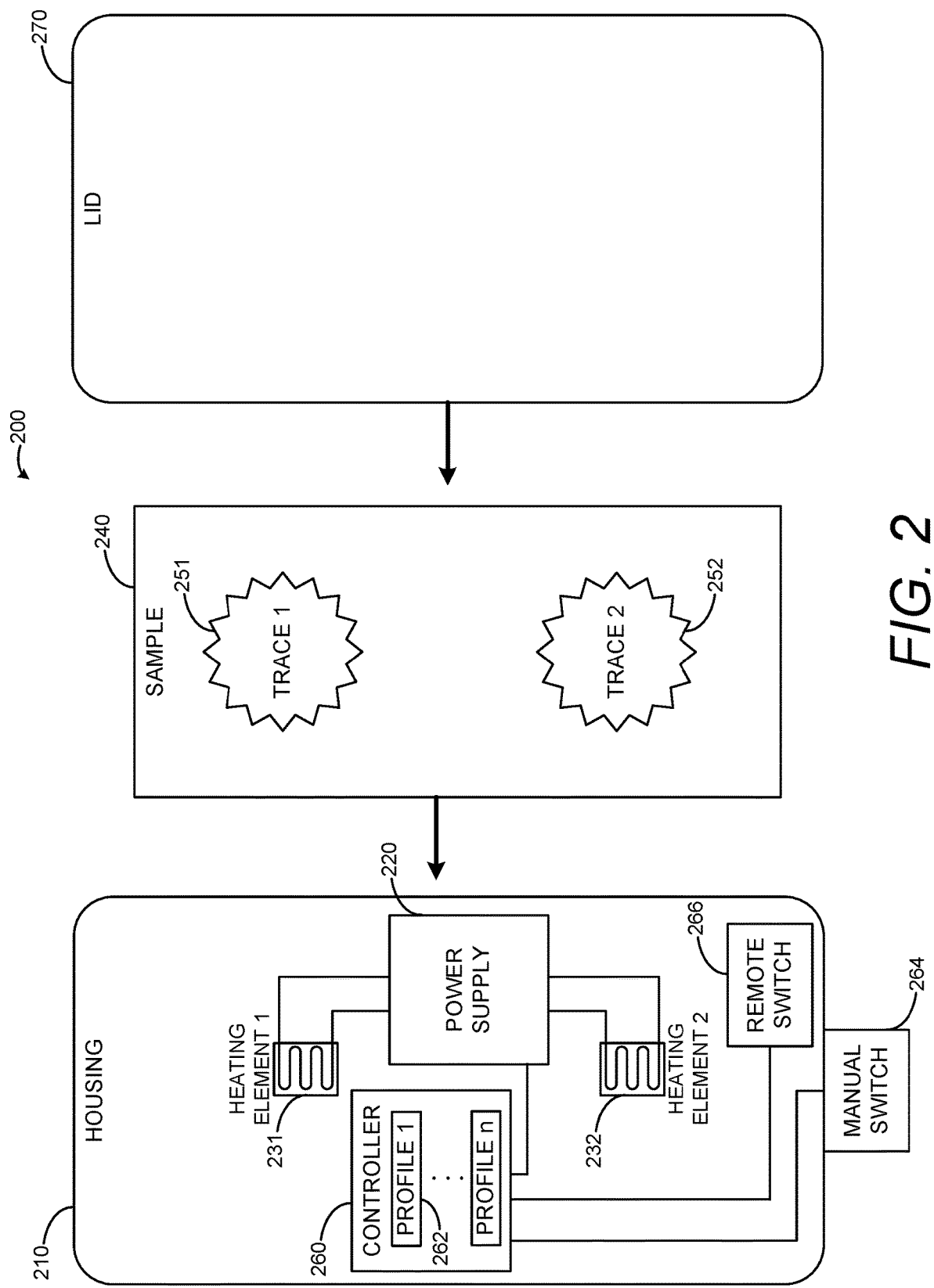
FIG. 2 illustrates a device including a controller and a plurality heating elements according to an example embodiment.

FIG. 2 illustrates a device 200 including a controller 260 and a plurality heating elements 231, 232 according to an example embodiment. The device includes housing 210 to support the sample 240 and the lid 270. The sample includes a plurality of traces 251, 252 of an explosive (two traces are shown for convenience, although more than two can be used). The housing 210 is configured to receive the sample 240 and the lid 270. The housing 210 includes a power supply 220, and a controller 260 including a plurality of profiles 262. The housing 210 also includes a manual switch 264 and a remote switch 266. In another embodiment, the housing 210 and other features can be dimensioned to serve as a wand configuration.

Two heating elements 231, 232 are illustrated, to selectively heat and generate vapor from two corresponding traces 252, 252 of the sample 240. In other embodiments, a grid of more than two heating elements are provided, to selectively activate a corresponding grid of traces deposited on the sample. Different heating elements are independently activated according to independent heating profiles, but also can be activated and/or controlled simultaneously. In the illustrated embodiment, the first heating element 231 is configured to generate a first vapor of a first ingredient from first trace 251, and a second heating element 232 is configured to generate a second vapor of a second ingredient from second trace 252 different than the first ingredient. In another embodiment, the sample 240 can include a single trace that spans the sample 240 such that the same trace is heated by both heating elements 231. Accordingly, the device 200 can use both heating elements 231, 232 to simultaneously generate two different vapors of the same trace.

The manual switch 264 is provided as a mechanical toggle switch, which can be manually operated to turn on and off one or more of the heating elements 231, 232. The remote switch 266 is a remote triggering mechanism to enable remote activation of the controller and/or one or more of the heating element(s) 231, 232. Although the switches 264, 266 are illustrated for convenience coupled directly to the controller 260, the switches 264, 266 can be coupled directly to the power supply 220 and/or the heating elements 231, 232. In an example, the remote switch 266 is a 433 megahertz radio frequency remote having a range of over 200 feet. In other examples, the remote switch 266 can be based on wireless technologies such as Bluetooth, Wi-Fi, radio frequency identification (RFID), and the like.

The controller 260 enables various heating profiles 262 for use in controlling heat application by the heating element (s) 231 and/or 232. Heating profiles 262 enable gradual or rapid temperature increases, or various other timing, temperature, and/or heating variations. For example, the controller 260 can enable a delay before activating the heating elements 231, 232, according to a profile 262. As used herein, the term profile contemplates a customizable script to direct operation of the controller and the power supply 220 and/or heating elements 231, 232. Additionally, the term profile contemplates the use of a corresponding timer, heat sensor, logic devices, or other circuit elements to automatically generate a desired behavior, without the need for particular scripts or other list of instructions or programming. In an example, a pulse generator circuit element is included in the controller, to generate controllable pulses of heat.

The device 200 applies a rate and duration of heat according to at least one selectable heating profile 262, e.g., corresponding to a type of the explosive and a characteristic of the at least one ingredient such as molecular weight and vapor pressure of the at least one ingredient. In an example, the controller can apply a series of profiles 262, e.g., to generate a variety of different vapors during a canine training session. A particular explosive compound, or a particular ingredient of the explosive compound, can be selectively targeted by the controller according to the profiles 262.

Alternatively, an embodiment can use a particularly configured circuitry, heating element, and/or power supply, without a controller, to generate a target temperature that targets a particular ingredient as a technique to implement a profile. For example, the first heating element 231 can be used to apply a first profile, and the second heating element 232 can be used to apply a second profile, by virtue of different characteristics of the heating elements themselves, even when manually connected to the power supply via manual switch 264. In another example, the heating elements 231, 232 can be the same as each other, but can be operated according to different profiles by, e.g., manually connecting the first heating element 231 to a first power supply (e.g., a single 9V battery), and by manually connecting the second heating element 232 to a second power supply (e.g., the single 9V battery in series with a second 9V battery), via manual switch 264 (e.g., a three-position toggle switch operable between off, profile 1, and profile 2). A profile 262 also can include time delays, such as a delay before activating a heater, or a delay between one heating application and another heating application.

A heating profile 262 also can be used to selectively generate a specific vapor, or otherwise be customized for a particular type of trace. For example, the heating profile 262 can be used to operate the heater(s) 231 and/or 232 to generate a vapor of one ingredient of the explosive, while not generating other vapors of other ingredients of the explosive. As described above, a trace 251, 252 of the explosive can involve multiple ingredients and corresponding vapors. A heating profile 262 can apply a lower intensity heat for a first duration, using a temperature below a threshold temperature, to vaporize some ingredients but not all ingredients. After the first duration, the profile can then apply a more intense temperature, high enough to vaporize other ingredients. In an example, the heating profile 262 can apply a heat below 100 degrees Celsius (C) for five minutes, and then apply a heat above 120 degrees C. for ten minutes.

Accordingly, profiles 262 can be used for many different applications. The device 200 can offer a menu of settings, and select profiles accordingly. Thus, in an example embodiment, the heating profile is selectable according to a type of canine training environment, such as a dynamic vs static hide. The heating profile is selectable according to a type of canine, such as a canine trained to alert to one particular ingredient or another, or a plurality of ingredients. The heating profile is adjustable according to varying power levels, e.g., allowing different power levels (e.g., difficulty levels) for a given profile. The heating profile is adjustable according to varying delay times prior to commencing heating. The controller 260 is configured to apply a profile 262 to thermally graduate and separate the various component ingredients of the traces 251, 252, e.g., by stepping through various temperatures to target increasing molecular weights/vapor pressures, to identify what ingredients a canine responds to, to identify how the canine was trained to alert, in real-world settings such as live passenger screening. Accordingly, it is possible to step through each ingredient in turn, to see if a canine alerts to the vapor of that particular ingredient, then moving on to the next ingredient.

The heating profile 262 includes a solvent removal mode, to apply heat to vaporize solvents of the trace to remove the solvents from the sample. The heating profile includes a condensation removal mode, to apply heat sufficient to remove condensation from the device. For example, operating the device may cause condensation to accumulate on the lid 270. Thus, a subsequent operation may be negatively influenced by the presence of the condensation. Accordingly, during, prior to and/or subsequent operation, the device 200 can apply heat at a temperature and duration sufficient to vaporize the condensation, so that operations are free of condensation.

The various features of the device 200 enable the heating elements to be operated by a user or coordinator, to turn on the heating element(s) via the manual switch 264 or the remote switch 266, continuously or for a designated period of time prior to, during, or subsequent to a canine training session. The controller 260 also can be used to operate the device 200, to prepare the sample prior to a training session, to apply a heating profile 262 during a training session, and to prepare the device subsequent to a training session. For example, prior to a training session, the device can heat the sample 240 to remove a solvent used to apply the traces 251, 252 to the sample 240.

Figure 3:
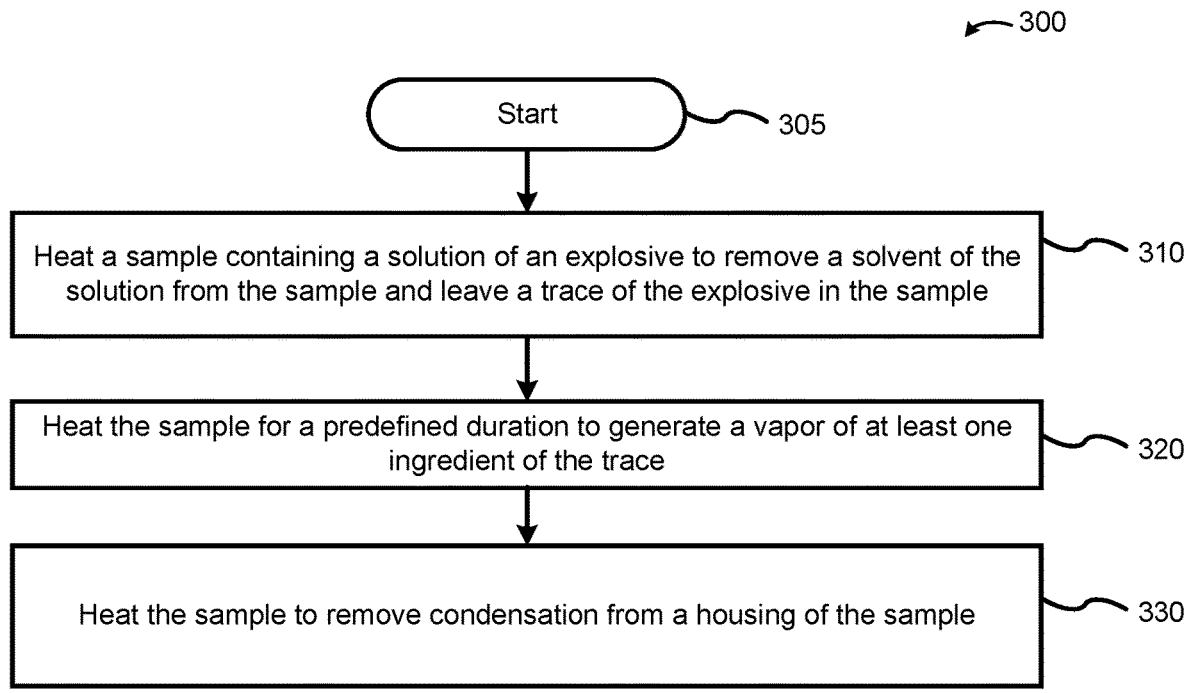
FIG. 3 illustrates a method of heating a sample to generate a vapor according to an example embodiment.

FIG. 3 illustrates a method 300 of heating a sample to generate a vapor according to an example embodiment. In block 310, a sample containing a solution of an explosive is heated to remove a solvent of the solution from the sample and leave a trace of the explosive in the sample. For example, RDX can be dissolved in a mixture of solvents. The resulting solution can be applied to a fiberglass sample, and heated at low temperature to remove the solvents. A similar approach can be used to remove other ingredients, such as other low molecular/high vapor pressure compounds, to further isolate particular ingredients for subsequent canine training. In block 320, the sample is heated for a predefined duration to generate a vapor of at least one ingredient of the trace. For example, the remaining trace can be heated at a medium heat, higher than a low heat used to vaporize the solvents, to generate a vapor of the target ingredient, to test whether a canine can alert to the target vapor, without being distracted by vapors of other ingredients. In block 330, the sample is heated to remove condensation from a housing of the sample. For example, the device can generate the RDX vapor for an extended period of time, which can cause condensation to accumulate on housing walls, a lid, or an aperture of the lid. The device can then be operated in a condensation removal mode, to generate heat sufficient to warm the device and/or condensation to cause the condensation to be removed.

In another example method, a device including a housing containing a sample with a trace of an explosive is placed in a canine training environment. Because of the portability of the example devices, the method is not limited to laboratory environments, and can be applied to dynamic or static training sessions with live decoys in real-world situations. The hidden device can be activated manually by a user upon hiding, or can be remotely activated by a coordinator unbeknownst to the user, or activated according to a timer or profile after being hidden. The sample is heated to generate a vapor of at least one ingredient of the trace. A canine can be observed in the training session to determine whether the canine alerts to the housing.

While a number of example embodiments of the present invention have been described, it should be appreciated that the present invention provides many applicable inventive concepts that can be embodied in a wide variety of ways. The example embodiments discussed herein are merely illustrative of ways to make and use the invention and are not intended to limit the scope of the invention. Rather, as will be appreciated by one of skill in the art, the teachings and disclosures herein can be combined or rearranged with other portions of this disclosure and the knowledge of one of ordinary skill in the art.

Terms and phrases used in this document, unless otherwise expressly stated, should be construed as open ended as opposed to closed—e.g., the term "including" should be read as meaning "including, without limitation" or the like; the term "example" is used to provide example instances of the item in discussion, not an exhaustive or limiting list thereof; the terms "a" or should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Furthermore, the presence of broadening words and phrases such as "one or more," "at least," "but not limited to," or other similar phrases, should not be read to mean that the narrower case is intended or required in instances where such broadening phrases may be absent. Any headers used are for convenience and should not be taken as limiting or restricting. Additionally, where this document refers to technologies that would be apparent or known to one of ordinary skill in the art, such technologies encompass those apparent or known to the skilled artisan now or at any time in the future.

What is claimed is:

1. A canine training device comprising:
    a portable housing to support a sample including a trace of an explosive, the portable housing sized to be handheld and carried on-the-move for training sessions with canines;
    a portable power supply coupled to the portable housing;
    a portable heating element coupled to the portable housing and configured to use power from the portable power supply to heat the sample to generate a vapor of at least one ingredient of the trace; and
    a controller coupled to the portable housing and configured to enable selecting from a plurality of selectable heating profiles including a first heating profile that, when selected, enables a delay before the controller activates the portable heating element, and a second heating profile that, when selected, causes the controller to direct the portable heating element to apply heat according to a solvent removal mode that vaporizes a solvent of the trace sufficient to disperse the solvent from the sample and leave the trace of the explosive in the sample, prior to the controller directing the portable heating element to generate the vapor of the at least one ingredient of the trace.

2. The canine training device of claim 1, further comprising a manual switch coupled to the portable housing and configured to selectively cause the portable heating element to apply heat to the sample.

3. The canine training device of claim 1, further comprising a remote switch configured to be remotely triggered to cause the portable heating element to selectively apply heat to the sample.

4. The canine training device of claim 1, wherein the heating profile is selectable based on the controller offering a menu of settings to allow for selection of a type of the explosive and a characteristic of the at least one ingredient.

5. The canine training device of claim 4, wherein the characteristic includes at least one of molecular weight and vapor pressure of the at least one ingredient.

6. The canine training device of claim 1, wherein the heating profile is selectable based on the controller offering a menu of settings to allow for selection of a targeted one of the at least one ingredient of the explosive, to generate a vapor of the targeted one of the at least one ingredient of the explosive, while not generating at least one other vapor of at least one other ingredient of the explosive.

7. The canine training device of claim 1, wherein the heating profile is selectable based on the controller offering a menu of settings to allow for selection of a canine training environment.

8. The device of claim 1, wherein the heating profile is selectable based on the controller offering a menu of settings to allow for selection of a type of a canine.

9. The device of claim 1, wherein the heating profile is adjustable based on the controller offering a menu of settings to allow for selection of a power level.

10. The device of claim 1, wherein the heating profile is adjustable based on the controller offering a menu of settings to allow for selection of a delay time relative to commencing heating.

11. The device of claim 1, wherein the heating profile includes a condensation removal mode that, when selected, enables the controller to apply heat sufficient to remove condensation from the device prior to generating the vapor of the at least one ingredient.

12. The device of claim 1, wherein the portable heating element includes a first heating element configured to generate a first vapor, and a second heating element configured to generate a second vapor different than the first vapor.

13. The device of claim 1, wherein the portable housing includes a lid.

14. The apparatus of claim 1, wherein the at least one selectable heating profile comprises a plurality of circuit elements and logic devices to operate the portable power supply and the portable heating element, to generate desired behavior for the solvent removal mode.

15. The apparatus of claim 1, wherein the portable housing is a static-dissipative polypropylene container having dimensions of 5.5 inches wide by 2.75 inched deep by 1.5 inches high.

16. The apparatus of claim 1, wherein the portable housing is a sleeve-style portable housing to configure the apparatus as a handheld wand unit.

17. The apparatus of claim 1, wherein the portable power supply comprises a first battery and a second battery, the controller being configured to selectively activate the portable heating element according to the plurality of selectable heating profiles, using the first battery alone, the second battery alone, or a combination of the first battery and the second battery to selectively power the portable heating element.

18. The apparatus of claim 1, wherein the plurality of selectable heating profiles includes a third heating profile that applies heat below 100 degrees Celsius (C) for five minutes, and then applies heat above 120 degrees C. for ten minutes, for training a canine to alert to a first ingredient, corresponding to generating a first ingredient vapor at 100 degrees C., and to alert to a second ingredient, corresponding to generating a second ingredient vapor at 120 degrees C.

19. The apparatus of claim 1, wherein the controller is configured to apply at least two profiles of the plurality of selectable heating profiles in series, to generate a corresponding at least two different vapors during a canine training session.

* * * * *